United States Patent [19]
Sangokoya

[11] Patent Number: 6,013,820
[45] Date of Patent: Jan. 11, 2000

[54] ALKYLALUMINOXANE COMPOSITIONS AND THEIR PREPARATION

[75] Inventor: Samuel A. Sangokoya, Baton Rouge, La.

[73] Assignee: Albemarle Corporation, Richmond, Va.

[21] Appl. No.: 09/040,874

[22] Filed: Mar. 18, 1998

[51] Int. Cl.$^7$ ................................. C07F 5/06; C07F 17/00
[52] U.S. Cl. .......................... 556/187; 556/179; 556/180; 502/103; 502/117; 502/152; 526/160; 526/943
[58] Field of Search ...................................... 556/179, 180, 556/187; 502/103, 117, 152; 526/160, 943

[56] References Cited

U.S. PATENT DOCUMENTS

| | | | |
|---|---|---|---|
| 3,300,458 | 1/1967 | R.M. Manyik et al. | 260/88.2 |
| 4,514,555 | 4/1985 | Taniguchi et al. | 528/9 |
| 4,908,463 | 3/1990 | Bottelberghe | 556/179 |
| 5,728,855 | 3/1998 | Smith et al. | 556/179 |

FOREIGN PATENT DOCUMENTS

| | | |
|---|---|---|
| 9714699 | 4/1997 | WIPO. |
| 9723288 | 7/1997 | WIPO. |

OTHER PUBLICATIONS

Eisch, John J., "Aluminum" Chapter 10, Comprehensive Organometallic Chemistry II, vol. 1, 1995, pp. 431–502.

Mole, et al., "Exhaustive C–Methylation of Carboxylic Acids by Trimethylaluminum: A New Route to t–Butyl Compounds", Aust. J. Chem., 1974, vol. 27, pp. 1665–1672.

Mole, et al., "Exhaustive C–Methylation of Ketones by Trimethylaluminum", Aust. J. Chem., 1974, vol. 27, pp. 1655–1663.

Mole, et al., "C–Methylation of Alcohols by Trimethylaluminum", Aust. J. Chem., 1974, vol. 27, pp. 1639–1653.

Mole, et al., "Hemi–Alkoxides From Reactions of Trimethylaluminum With Aldehydes or Ketones", Aust. J. Chem., 1970, vol. 23, pp. 715–724.

*Primary Examiner*—Porfirio Nazario-Gonzalez
*Attorney, Agent, or Firm*—Philip M. Pippenger

[57] ABSTRACT

The reaction between an alkylaluminum compound such as trimethylaluminum and carbon dioxide or an organic carbonyl reagent such as benzoic acid or benzophenone is facilitated and accelerated by contacting these reactants in the presence of an inert organic solvent/diluent and a catalytic quantity of water. The process is preferably conducted using continuous feeds of the components to the reaction zone. The proportions of (I) and (ii) fed to the reactor are maintained such that there are about 1.4 to about 2.2 moles of alkylaluminum per mole of oxygen atoms as $CO_2$ or the organic carbonyl reagent, and the weight ratio of aluminum alkyl to the solvent/diluent is preferably in the range ca. 20:80 to ca. 60:40. Polyalkylaluminoxanes formed in the process can have better solubility in paraffinic or cycloparaffinic hydrocarbons, and also greater storage stability.

59 Claims, 2 Drawing Sheets

ALKYLALUMINOXANE COMPOSITIONS AND THEIR PREPARATION

BACKGROUND

Hitherto, hydrocarbylaluminoxanes were prepared by careful addition of water, at low temperatures, as a reagent to a solution of trialkylaluminum. Such processes have been the subject of several patents; for example, U.S. Pat. No. 3,300,458 to Manyik etal., U.S. Pat. No. 4,722,736 to Edwards et al., U.S. Pat. No. 4,730,071 to Schoenthal et al., and U.S. Pat. No. 4,908,463 to Bottelberghe.

Several alkylaluminoxanes including mixtures of aliminoxanes, have been employed as co-catalysts in olefin polymerization. However, the most useful and widely used co-catalyst, especially in single-site or metallocene-based olefin polymerization is methylaluminoxane (MAO). Despite the importance of methylaluminoxane as co-catalyst, structural characterization has largely been hampered by limited solubility and solution instability. In solution, methylaluminoxane is believed to undergo rapid and significant dynamic equilibrium between several aluminoxane species including residual trimethylaluminum (TMA). For a relatively recent review of several aspects of structural advances involving methylaluminoxane and aluminoxanes in general, see Pasynkiewicz, *Polyhedron*, 1990, 9, 429.

T. Mole and co-workers have described the chemistry of exhaustive methylation of alcohols, ketones, and carboxylic acids by treatment with trimethylaluminum as early as 1974. See *Aust. J. Chem.*, 1974, 27, 1665. Although indicating that the by-product of these reactions was an aluminoxane, these MAO by-products were destroyed by hydrolysis, because those authors were more interested in the methylated hydrocarbons produced in the reactions. A recent review by J. J. Eisch, *Comprehensive Organometallic Chemistry II*, Vol. 1, 1995, 452, also confirmed that the exhaustive C-methylation chemistry described by T. Mole and co-workers must have been accompanied by aluminoxane formation. Eisch further added that such compositions are not suitable for catalytic olefin polymerization because of the presence of potentially deactivating Lewis base in the reaction product (see equation 59 of this Eisch review).

In published patent application WO 97/14699 (Apr. 24, 1997), G. M. Smith et al. describe formation of modified polyalkylaluminoxane compositions by initially treating a composition comprising trialkylaluminum with a reagent containing a carbon-oxygen double bond, followed by hydrolysis of the resulting composition. Reagents with a carbon-oxygen double bond referred to are carbon dioxide, a ketone, an aldehyde, a carboxylic acid, a carboxylic acid ester, a carboxylic acid anhydride, and a carboxylic acid amide. The products are indicated to contain oligomeric alkylaluminoxane and moieties having the structure —OC(R)$_3$, where R is hydrocarbyl, such as lower alkyl, such as methyl.

More recently, in published patent application, WO 97/23288 (Jul. 3, 1997) G. M. Smith et al. describe a non-hydrolytic (without water) preparation of polyalkylaluminoxane compositions by essentially using the method of Mole et al. Thus trimethylaluminum is treated with certain oxygen-containing organic compounds such as an alcohol, a ketone, or a carboxylic acid to form aluminoxane and C-methylated hydrocarbons. Reaction with carbon dioxide is also referred to in this Smith et al. application. However, unlike Mole et al., the methylaluminoxane composition product was not destroyed by hydrolysis.

The latter published patent application by Smith et al. uses similar conditions to those of Mole et al. characterized by long reaction times and high temperatures. Several publications have described the enhanced acceleration of gel formation process in methylaluminoxane solution by prolonged heating, especially at high temperature; including, for example, U.S. Pat. No. 5,329,032 to N. H. Tran et al. and Japanese Patent Publication No. 49293/92.

While it is conceivable that viable preparation of MAO using the method of Mole et al. is possible, it would be highly desirable to find an MAO production process capable of using milder conditions in order to ensure the integrity of the resulting methylaluminoxane composition as hydrocarbon-soluble and storage-stable material. Commercial methylaluminoxane products are often transported to distant overseas destinations requiring several weeks of transit. It is therefore important to avoid gel formation or excessive viscosity increases that could hamper removal or transfer of the aluminoxane products from tank to tank. Furthermore, transfer of methylaluminoxane solution from a storage tank to polymerization reactor is facilitated by the absence of gels, solid-forming precipitates, or high viscosity liquids due to storage instability of the solution.

BRIEF SUMMARY OF THE INVENTION

It has now been found possible to form novel aluminoxanes and especially methylaluminoxane compositions having high solubility in a number of hydrocarbon solvents and also having increased resistance to gel formation. It has also been found possible to produce such novel aluminoxanes, including novel methylaluminoxane compositions, with high efficiency and under milder conditions than those advocated by the prior art.

In accordance with this invention, aluminoxanes are produced by water-catalyzed reactions of one or more alkylaluminum compounds ($R_n AlH_{3-n}$, where R is an alkyl group, and n is a number in the range of 1 to 3), especially trimethylaluminum (TMA), and organic carbonyl derivatives and/or carbon dioxide in the presence of a suitable amount of a suitable organic solvent, preferably in an aromatic hydrocarbon solvent, or a mixture of any two or more suitable hydrocarbon solvents, at moderate reaction conditions.

Thus pursuant to one embodiment of this invention there is provided a process which comprises mixing together in the presence of a liquid organic solvent (preferably an inert hydrocarbon solvent) and in the presence of a catalytic quantity of water, (i) an aluminum alkyl (e.g., a trialkylaluminum or a mixture thereof or an alkylaluminum hydride or a mixture thereof), and (ii) a reagent selected from (a) an organic carbonyl group-containing compound or mixture thereof, or (b) carbon dioxide, or (c) a mixture of at least one organic carbonyl group-containing compound and carbon dioxide, such that an alkylaluminoxane product is produced. For convenience, the reagent selected from (a) an organic carbonyl group-containing compound or mixture thereof, or (b) carbon dioxide, or (c) a mixture of at least one organic carbonyl group-containing compound and carbon dioxide is sometimes hereinafter referred to individually or collectively as the "carbonyl reagent", and the organic carbonyl group-containing compound or mixture thereof is sometimes hereinafter referred to individually or collectively as the "organic carbonyl reagent". The catalytic quantity of water and the carbonyl reagent are co-present before (i) and (ii) are mixed together in the presence of an inert organic solvent. That is, the trialkylaluminum and catalytic quantity of water are brought into contact with each other at the same time contact is being established between the trialkylaluminum and the carbonyl reagent. The catalytic quantity of water apparently serves at least in part as a reaction initiator and reaction accelerator, and preferred modes of addition involve introducing (a) the aluminum alkyl, most preferably dissolved in a suitable solvent or reaction diluent, to (b) a preformed mixture of the carbonyl reagent and the catalytic quantity of water, or vice versa, i.e., addition of (b) to (a). Particularly preferred modes of addition involve concurrent continuous feeds of (a) and (b) to the reactor.

In order to achieve rapid water-catalyzed reaction pursuant to this invention it is desirable to ensure that the weight ratio of aluminum alkyl to liquid organic solvent (e.g., inert hydrocarbon solvent) fed to the reaction mixture is at least 10:90 and preferably is in the range of about 20:80 to about 60:40. In the case of trimethylaluminum (TMA), a more preferred weight ratio (TMA:solvent) is in the range of about 30:70 to about 55:45, with weight ratios in the range of about 40:60 to about 50:50 being particularly preferred. For example, it is especially desirable to feed to the reactor a 50 wt % solution of TMA in a hydrocarbon solvent such as toluene or xylene with no other organic solvent being used in the reaction. It will be understood that the solvent in these ratios does not include organic carbonyl reagent.

The preferred carbonyl reagents are organic carbonyl reagents, and especially organic carbonyl-group-containing compounds deprived of an enolizable carbon center. The reaction can be carried out in paraffinic, cycloparaffinic and/or aromatic hydrocarbon solvents. In preferred embodiments the reaction is carried out in an aromatic solvent (e.g., toluene, xylene, ethylbenzene, etc.) or in a mixture of a predominately aromatic hydrocarbon solvent together with a minor amount by weight of one or more paraffinic and/or cycloparaffinic hydrocarbon solvents.

Preferred feed streams are a preformed solution of aluminum trialkyl, especially trimethylaluminum, in an inert liquid solvent, especially an inert liquid aromatic hydrocarbon solvent, and a preformed mixture of a catalytic quantity of water and an organic carbonyl reagent, especially benzoic acid and/or one or more alkyl-substituted benzoic acids or benzophenone and/or one or more alkyl-substituted benzophenones.

Proportions of the feeds used are such that there are about 1.4 to about 2.2 moles of aluminum alkyl per mole of oxygen atoms in the organic carbonyl reagent, and in the range of about 0.001 to about 0.1 mole of water per mole of the organic carbonyl reagent.

The practice of this invention has resulted in considerable reduction in both the reaction time and reaction temperature. In addition, the resulting products exhibit better hydrocarbon solubility and storage stability compared to prior art products.

Another embodiment of this invention is an aluminoxane composition produced using the above water-catalyzed process.

Without being bound by theory, the general reaction scheme of this invention may be described as involving abstraction of oxygen atoms from the carbonyl reagent in order to form Al—O—Al groups, which are believed to be the basic composition of aluminoxanes. However this mechanism appears to be highly complex. Proton NMR analyses of the reaction mixtures during the progress of the reaction indicate that upon contacting the carbonyl reagent and aluminum alkyl in the presence of the catalytic quantity of water and using stoichiometry described above, a very complex mixture of reaction intermediates or intermediate products is initially formed and transformed into the desired final aluminoxane product.

A surprising feature of this invention is that when the reaction is carried out in an inert liquid aromatic hydrocarbon solvent or diluent, the transformation of the intermediate products formed upon contacting the carbonyl reagent and aluminum alkyl in the presence of the catalytic quantity of water, to the desired aluminoxane product can be achieved rapidly, and without supplying additional heat or adding an aluminoxane catalyst to the reaction mixture containing intermediate products. Prior art procedures involve heating and/or adding an aluminoxane catalyst to an intermediate reaction mixture formed under anhydrous conditions. While such procedures can be employed if desired, by avoiding use of such prior art procedures, this invention makes it possible to form a superior product composition which is less susceptible to hydrocarbon insolubility and storage instability with respect to gel or solid formation, or excessive increases in viscosity.

It is of interest to note that conventional prior art preparations of methylaluminoxane by water hydrolysis of trimethylaluminum in aromatic solvents usually result in substantial yield loss due to solid by-product formation. Moreover, in prior practice, higher yield loss is generally observed when the reaction is carried out in aliphatic hydrocarbons and this is certainly economically unacceptable. This invention, in contrast, enables the achievement of comparable high aluminoxane yields in suitable hydrocarbon solvents, including paraffins and cycloparaffins, as well as aromatics.

In a preferred embodiment, this invention most especially relates to formation of methylaluminoxane by a hydrolytically catalyzed reaction of trimethylaluminum and a non-enolizable organic carbonyl reagent at moderate reaction temperature conditions.

Particularly preferred embodiments are set forth in appended claims 27–55 in this application as filed. These embodiments involve (a) continuous feeds to a reactor of an aluminum trialkyl or alkyl aluminum hydride, or both, an organic carbonyl reagent, a catalytic quantity of water, and optionally but preferably, at least one inert organic solvent or diluent such that a reaction mixture comprising alkylaluminoxane or a intermediate precursor thereof is being produced in the reactor, and (b) continuously or periodically withdrawing reaction mixture from the reactor at a rate sufficient to enable the continuous feeds of (a) into the reactor to be maintained. Typically at least one inert organic solvent or diluent is included in these continuous feeds, and at least a portion thereof is usually fed in the form of a solution of the aluminum trialkyl and/or alkyl aluminum hydride in the inert solvent. Likewise, it is desirable to feed the water in admixture with the carbonyl reagent.

The above and other features and embodiments of this invention will be still further apparent from the ensuing description and appended claims.

FURTHER DETAILED DESCRIPTION OF THE INVENTION

Carbonyl Reagent

Figure 3:
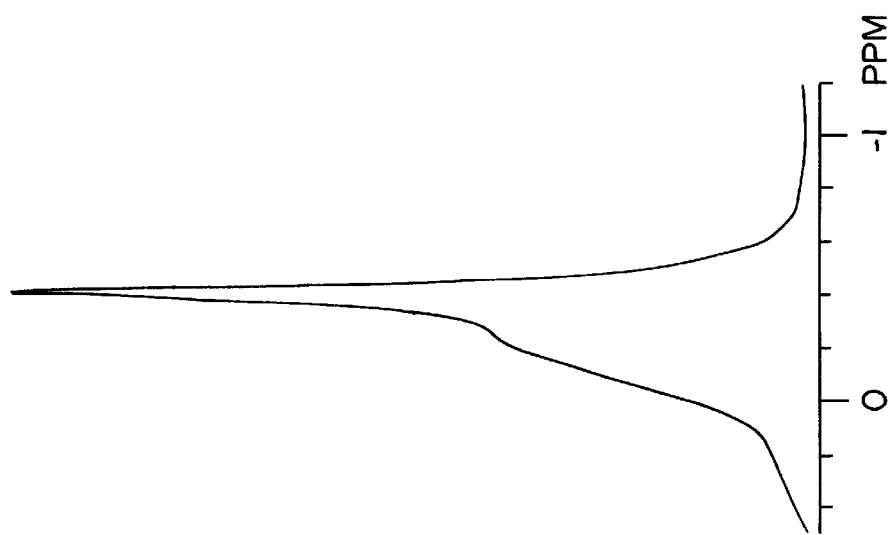
FIG. 3 is the Al—CH$_3$ region of a proton NMR spectrum of a typical polymethylaluminoxane product composition that has been subjected to further heating at 80° C. The broad peaks of this spectrum illustrate the lack of uniformity and non-homogeneity of the product. This spectrum, as compared to that of FIG. 2, shows the deleterious effects of exposure of the products to high temperatures at any stage in their synthesis or storage.

Any carbonyl-group-containing compound is potentially useful carbonyl reagent in accordance with the present invention provided it is free of functionality that would materially interfere with the desired reaction. Thus as regards organic compounds, it is deemed potentially possible to make use of aldehydes, ketones, carboxylic acids, carboxylic acid esters, carboxylic acid anhydrides, carboxylic acid amides, or like carbonyl-group-containing organic compounds. Other acceptable functional groups that may also be present in the organic carbonyl reagent include ether oxygen atoms, hydroxyl groups, tertiary amino groups, etc. The presently preferred carbonyl reagents are ketones and carboxylic acids, as compounds of these types have been found highly suitable in actual practice. A mixture of carboxylic acids or a mixture of ketones and also a mixture of one or more carboxylic acids with one or more ketones can be used, especially if such mixtures result in a soluble or liquid reagent. Typically the carbonyl reagent will contain up to about 40 carbon atoms in the molecule. As noted above, carbon dioxide can be used as the carbonyl reagent, either alone or in combination with one or more organic carbonyl reagents. However use of organic carbonyl reagents is preferred over use of carbon dioxide.

Examples of suitable carbonyl reagents include such carboxylic acids as benzoic acid, methylbenzoic acid, ethylbenzoic acid, 1,4-phenylene dicarboxylic acid, ascorbic acid, formic acid, acetic acid, propionic acid, hexanoic acid, octanoic acid, oxalic acid, malonic acid, succinic acid, terephthalic acid, phthalic acid, homoterephthalic acid, 4-hydroxybenzoic acid, ethylenediaminetetraacetic acid, diethylenetriaminepentaacetic acid, and the like. Typical ketones include acetone, methylethylketone, diethylketone, benzophenone, cyclohexanone, acetylacetone, ethyl acetoacetate, octyl acetoacetate, and the like. Typically the carboxylic acids will contain from one to about four carboxyl groups and up to about 24 carbon atoms in the molecule. The ketones will typically contain from one to three carbonyl groups and up to about 24 carbon atoms per molecule.

Particularly preferred organic carbonyl reagents are ketones or carboxylic acids that are deprived of an enolizable carbon center.

Aluminum Alkyl

Halogen-free aluminum alkyls constitute the other reactant used in the process. Suitable aluminum alkyls include trialkyl aluminum (R$_3$Al) or alkyl aluminum hydrides (R$_n$AlH$_{3-n}$ where n is in the range of 1 to 2). Each alkyl group typically will contain up to about 20 carbon atoms, and these alkyl groups are normally primary alkyl groups. The alkyl groups may be linear (i.e., straight chain), branched or cyclic or combinations of these, with the straight chain alkyl groups being preferred. Trialkyl aluminum compounds are preferred, and of these trimethylaluminum is most preferred. Mixtures of two or more aluminum trialkyls or of two or more alkyl aluminum hydrides can be used, as well as mixtures of one or more aluminum trialkyls and one or more alkyl aluminum hydrides.

Solvent/Reaction Diluent

Non-complexing organic solvents can be used as solvents or reaction diluents, if desired. While hydrocarbon solvents are preferred, it is possible to conduct the reaction in certain other organic solvents such as inert liquid hydrocarbylsilanes, R$_4$Si where R is alkyl or aryl. Suitable hydrocarbon liquid reaction solvents or diluents include (i) one or a mixture of paraffinic hydrocarbons (a.k.a., straight or branched chain alkanes), (ii) one or a mixture of cycloparaffins (a.k.a., cycloalkanes and/or alkyl-substituted cycloalkanes), (iii) one or a mixture of aromatic hydrocarbons, and (iv) a mixture of any two or all three of (i), (ii), and (iii). Of the liquid hydrocarbon solvents one or more aromatic hydrocarbons, or a mixture of at least 50% by weight of one or more aromatic hydrocarbons and no more than 50% by weight of one or more paraffinic and/or cycloparaffinic hydrocarbons are preferred. It is also possible to employ predominately aromatic hydrocarbon mixtures containing one or more liquid aliphatic monoolefins such as 1-olefins (1-hexene, 1-octene, 1-decene, etc.), in the solvent medium, especially when using an alkyl aluminum hydride as the aluminum alkyl reactant, as this can result in the formation in situ of aluminum trialkyls.

Based on experimental work conducted to date, it appears that when the solvent used in the process is entirely a paraffinic solvent (e.g., heptane or octane) or a cycloparaffinic solvent (e.g., cyclohexane), the addition of a catalytic quantity of a preformed polyalkylaluminoxane such as solid MAO (i.e., solvent-free MAO) to the intermediate reaction product formed in a water-catalyzed reaction of this invention is highly advantageous, if not necessary, in order to form an aluminoxane product that has good solubility in paraffinic and cycloparaffinic hydrocarbon solvents as well as good storage stability. Moreover, the use of such solvent-free MAO ensures that no aromatic solvent is incorporated into an aliphatic solution of the MAO in situations where the presence of aromatic solvents is undesired.

Modes of Addition

In the practice of this invention the reaction is typically initiated in the presence of a catalytic quantity of water, i.e., an amount in the range of about 0.1 to 10 mole percent of the carbonyl reagent being used. Catalytic addition of water to the reaction mixture can be accomplished in any suitable manner. In one suitable procedure, a catalytic amount of water in the range of from 0.1 to 10 mole percent of the carbonyl reagent is added to the solution or slurry of the carbonyl reagent in a hydrocarbon solvent or diluent such as a paraffinic, cycloparaffinic and/or aromatic hydrocarbon solvent or diluent. Then the aluminum alkyl reactant such as trimethylaluminum is slowly added to the reaction mixture. This slow addition can be performed as a continuous slow addition or as an intermittent portionwise slow addition. Alternatively, the addition can in part be on a slow continuous basis and in part on a portionwise intermittent addition basis. The rate of addition should be such as to keep the reaction progressing at a suitable rate. It is desirable to thoroughly agitate the reaction mixture to ensure intimate contact between or among the reactants.

Another suitable procedure involves dissolving or suspending the carbonyl reagent in a wet solvent or diluent containing a catalytic amount of water, followed by controlled slow addition of the aluminum alkyl reactant, either continuously or intermittently, or in part continuously and in part intermittently, to the well-agitated reaction mixture. Still another way of introducing the catalytic quantity of water to initiate the reaction comprises using as the starting material a carbonyl reagent having a determined amount of water of crystallization. Likewise, a mixture of a carbonyl reagent free of water of crystallization and a small quantity of hydrated carbonyl reagent can be used, such that the hydrated carbonyl reagent introduces the catalytic amount of water necessary to catalyze the reaction with the aluminum alkyl reactant such as trimethylaluminum, resulting in a process with shorter reaction times and at moderate reaction temperatures compared to prior art processes. It is possible to carry out a controlled slow addition of the carbonyl reagent and a catalytic quantity of water concurrently to a solution of the aluminum alkyl.

In each of the above modes of conducting the process, the aluminum alkyl and catalytic quantity of water are brought into contact with each other at the same time contact is being established between the trialkylaluminum and the carbonyl reagent. In other words, the aluminum alkyl and the catalytic quantity of water are not brought into contact with each other before contact is established between the aluminum alkyl and the carbonyl reagent.

In particularly preferred embodiments the process utilizes the following modes of addition:

a) continuously feeding into a reactor (i) an aluminum trialkyl or alkyl aluminum hydride, or both, (ii) a carbonyl reagent or mixture thereof, (iii) a catalytic quantity of water, and optionally but preferably, (iv) at least one inert organic solvent or diluent such that a reaction mixture comprising alkylaluminoxane or a intermediate precursor thereof is being produced in the reactor; and b) continuously or periodically withdrawing reaction mixture from the reactor at a rate sufficient to enable the continuous feed of a) into the reactor to be maintained.

There are various ways by which such continuous feeds in a) can be effected and utilized. For example, the continuous feeds of a) can be maintained at the same time reaction mixture is being withdrawn periodically or continuously from the reactor. Alternatively, the reactor can be a suitably-sized large reactor or vessel into which the components of a) are continuously and concurrently fed until the reactor has been filled to a predetermined level with the resultant reaction mixture, at which time the feeds of a) are discontinued, and thereafter all or at least a portion of the reaction mixture is withdrawn from the reactor. In either such case reaction mixture withdrawn in b) is preferably cooled or allowed to cool to approximately room temperature and allowed to stand at ambient room temperature.

It will of course be understood and appreciated that the process of this invention should be carried out under an inert atmosphere, such as under a flow or blanket of inert gas such as nitrogen, argon, helium, neon, krypton, etc. When using a flow of inert gas it is possible to use the inert gas as a carrier of the catalytic quantity of water into a mixture of the aluminum alkyl and carbonyl reagent, preferably in a suitable solvent or diluent.

In each of the foregoing illustrative modes of carrying out the process of this invention, the aluminum alkyl can be employed neat (i.e., undiluted) but is preferably employed as a preformed solution in a suitable solvent such as toluene. The carbonyl reagent can be fed as a neat material or it can be pre-dissolved or pre-slurried in a suitable solvent or diluent. Likewise the water can be added in the form of a preformed mixture in a suitable diluent, preferably a hydrocarbon diluent or as a mixture with the carbonyl reagent.

It can be seen that, however it is carried out, the process of this invention involving water-catalyzed reactions is the antithesis of the non-hydrolytic preparation of aluminoxanes according to the teachings of published patent application WO 97/23288. Likewise, the process of this invention differs sharply from that of published patent application WO 97/14699 wherein a composition is initially formed non-hydrolytically and then the entire reaction mixture is subjected to hydrolysis. The present invention thus provides unique approaches to preparing novel methylaluminoxane compositions.

The catalytic quantity of water appears to serves at least in part as a reaction initiator and reaction accelerator, and therefore one preferred mode of addition involves introducing the aluminum alkyl to a preformed mixture of the carbonyl reagent and the catalytic quantity of water, most preferably in a suitable solvent or reaction diluent.

Reaction Conditions

In the practice of this invention at least two factors mutually cooperate with each other to significantly improve the process and product of the reaction of aluminum alkyl, e.g., trimethylaluminum, with carbonyl reagents; namely: (i) having a catalytic quantity of water present in the reaction mixture prior to or at essentially the same time as (e.g., no later than about 1–2 minutes after) the aluminum alkyl is first brought into contact with the carbonyl reagent, and (ii) use of about 1.4 to about 2.2 moles of aluminum alkyl per mole of oxygen atoms in the carbonyl reagent. These two factors are believed responsible for lowering the required reaction temperature from 100–300° C. to below 100° C. and also for reducing the reaction time from 24–48 hours to less than about 4 hours. Preferably, the reaction is carried out using up to 0.1 mole of water per mole of the carbonyl reagent, about 1.5 moles of trimethylaluminum per mole of oxygen atoms in the carbonyl reagent, and heating at 60 to 80° C. during a reaction period of about 2 to 4 hours after addition of the reactants and catalytic quantity of water to the reaction vessel.

Thus pursuant to this invention the rapidity of the reactions as induced or initiated by the catalytic quantity of water makes possible avoidance of the detrimental effect of prolonged heating on the properties of the resulting alkylaluminoxane products. Equally surprising, is the discovery that by using the catalytic quantity of water and the reactant proportions as described above in the immediately preceding paragraph, the transformation of the intermediate products to alkylaluminoxane compositions, preferably a polymethylaluminoxane composition, can be accomplished without application of heat to the reaction mixture. Thus, the reaction can be initiated at room temperature and continued during storage of the reaction mixture at ambient room temperature. As a result, this process further allows for a superior product composition which is less susceptible to hydrocarbon insolubility and storage instability with respect to gel and/or solids formation. Thus in certain preferred embodiments of this invention the reaction is performed adiabatically (i.e., only exothermic heat of reaction is utilized), and the temperature is kept below 100° C., and preferably is kept from exceeding about 80° C. Most preferably the temperature is kept below about 70° C.

In order to still further demonstrate the practice and advantages of this invention, the following Examples are presented for the purpose of illustration, and not limitation.

COMPARATIVE EXAMPLE

Preparation of Methylaluminoxane (MAO) by Non-Hydrolytic Method

This experiment serves to illustrate the non-hydrolytic method for preparing MAO as described by WO 97/23288. The reaction was carried out in anhydrous toluene solvent in order to ensure a non-hydrolytic process. Thus, benzoic acid (EZA, 5.4 grams, 0.04422 moles) was added slowly in small batches, under nitrogen atmosphere, to a solution of trimethylaluminum (TMA) (8 grams, 0.11097 moles) in anhydrous toluene (10 grams).

The reaction was quite exothermic with vigorous gas evolution. By calculation, each mole of oxygen atom in BZA was treated with about 1.25 moles of TMA. After the addition, the reaction mixture was heated at 80° C. for six hours before H-1 NMR confirmed the absence of transitional or intermediate products. The resulting product was a viscous yellowish oil and contained no solids. Surprisingly, attempts to dissolve the viscous oil product in NMR solvent ($C_6D_6$) clearly showed that the product was no longer completely miscible in additional hydrocarbon solvents as indicated by the inhomogeneity in the NMR spectrum. After keeping the product at room temperature, under nitrogen atmosphere, during a period of about two weeks, the yellowish color dissipated and solid/gel product resulted, indicating that the methylaluminoxane (MAO) made by this process could be associated with serious storage instability.

Examples 1–8 illustrate preparation of aluminoxanes by water-catalyzed reactions or the partial hydrolytic method of this invention. In Examples 1–8, the following general procedure was used.

General Procedure

All experiments were carried out under inert atmospheric conditions, using Schlenk glassware and vacuum line, in conjunction with an $N_2$ dry box. Solvents were dried using standard methods. Trialkylaluminum compounds ($R_3Al$) were obtained from stock solutions produced by Albemarle Corporation. The carbonyl reagents, viz., benzoic acid, benzophenone, acetic acid, etc., were obtained from Aldrich Chemical Company and used as received.

Example 1

Figure 2:
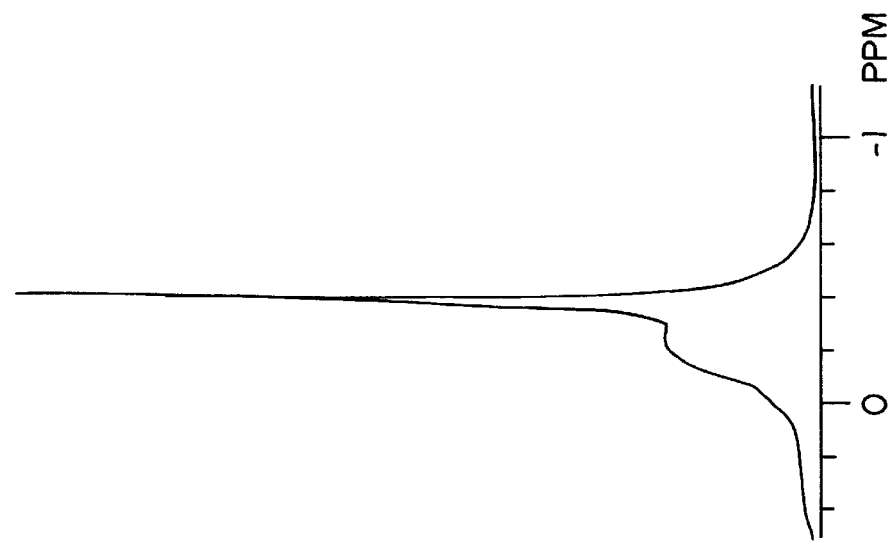
FIG. 2 is the Al—$CH_3$ region of a proton NMR spectrum of a typical polymethylaluminoxane product composition of this invention as formed in the process of this invention. This spectrum serves to illustrate the uniformity and homogeneity of such product compositions.
Figure 1:
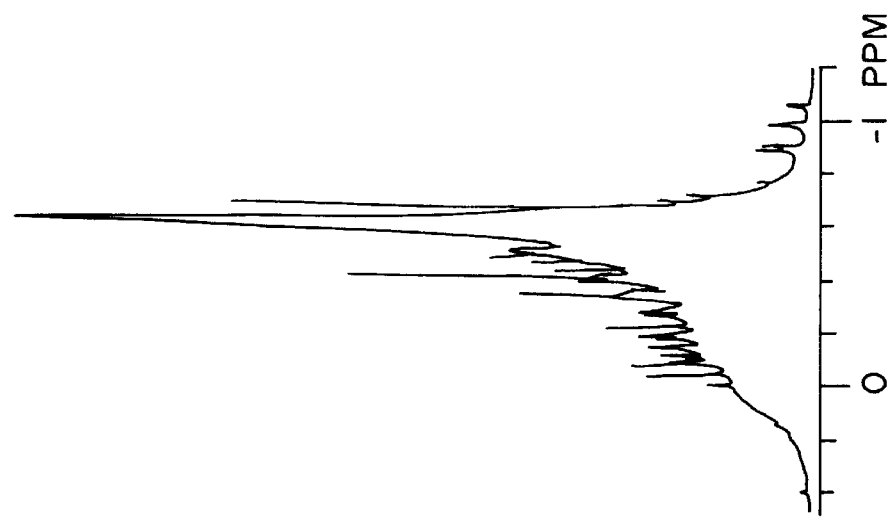
FIG. 1 is the Al—$CH_3$ region of a proton NMR spectrum of a typical intermediate reaction product mixture formed in the process of this invention. This spectrum serves to illustrate the complexity of such mixtures.

Benzoic acid (5.4 grams, 0.04422 mole) was suspended in toluene (20.5 grams). Water (0.08 gram, 0.004422 mole) was added. While stirring the mixture at room temperature, TMA (10.24 grams, 0.1420 mole) was slowly added. Total addition time was about one hour. The reaction was very exothermic with gas evolution. After addition, the mixture was stirred at room temperature during about one hour. Proton NMR showed several peaks in the Al—Me region, which is indicative of the presence of intermediate products. See FIG. 1. The mixture was then heated at 80° C. (oil bath) for about three hours to obtain a colorless solution. Proton NMR confirmed formation of MAO. The product mixed well with the NMR solvent as indicated by lack of inhomogeneity in the NMR spectrum. See FIG. 2. Therefore, this product showed good solubility in hydrocarbon solvent. The product was stored in a glass bottle under nitrogen and remained clear with no visible gel or solid formation even after eight weeks at room temperature.

Example 2

TMA (10.24 gram, 0.1420 mole) was allowed to react with a slurry of benzoic acid (5.4 grams, 0.04422 mole) in toluene (20.5 grams) containing water (0.16 gram, 0.008844 mole). The addition of an extra amount of water compared to Example 1 led to formation of some solid by-products, which were removed by filtration. The product was, however, just as soluble and storage stable as the product of Example 1.

Example 3

This reaction was carried out at higher concentration in the presence of 0.1 mole of water per mole of BZA. TMA (33.2 grams, 0.4605 mole) was allowed to react with a slurry of BZA (20 grams, 0.1638 mole) in toluene (70 grams) containing water (0.29 gram, 0.01638 mole), as described in Example 1. Pyridine titration showed that the clear, colorless products, according to this invention, contained 15–24 mole percent of the total aluminum as TMA. The solutions remained clear without visible gel or solid formation even after eight weeks. The TMA content of MAO prepared according to this process could be subsequently reduced either by distillation under vacuum or by reaction with small quantities of the carbonyl reagent. Some processes require a higher amount of TMA, in which case more TMA could be added to the product. Thus portions of the products were distilled under reduced pressure to obtain products having 10–20 mole percent of the total aluminum as TMA. Similarly, addition of more BZA to portions of the product led to formation of products having 6–12 mole percent of the total aluminum as TMA.

Example 4

A mixture of carboxylic acids was also used to illustrate the present invention, using toluene as the solvent. Thus, benzoic acid (3.05 grams, 0.025 mole) was added to acetic acid (1.5 grams, 0.025 mole). To this solution was then added water (0.09 gram, 0.005 mole). TMA (10.8 grams, 0.15 mole) was then slowly added to the mixture during about a one-hour period. The mixture was stirred to room temperature during another hour after addition. A slightly yellowish solution resulted after heating the mixture at 80° C. (oil bath) during about three hours. Proton NMR indicated an incomplete reaction due to extra peaks in the Al—Me region. Then solid MAO containing 5 millimoles of aluminum was added and the mixture heated at 80° C. for another two hours. The resulting clear solution was shown by NMR to be an MAO solution.

Example 5

To a slurry of benzoic acid (20 grams, 0.1637 mole) in cyclohexane (66 grams) was added water (0.29 gram, 0.01637 mole). Then TMA (35.4 grams, 0.4913 mole) was slowly added during a period of about one hour. The reaction was very exothermic with considerable gas evolution. The product was stirred at room temperature for about one hour after addition. After this, the mixture was heated at 80° C. (oil bath) for about three hours. Proton NMR suggested incomplete reaction by the presence of extraneous peaks in the Al—Me region. An aliquot of the intermediate product was transferred to another reaction vessel and heated at 100° C. for 6 hours. The resulting product was viscous and gelatinous. H-1 NMR showed total conversion to MAO. This product was found to be unstable with respect to solid and gel formation, thus illustrating the disadvantages of high temperature exposure. To the rest of the initial intermediate product was added a catalytic amount of solid MAO. The mixture was then heated at 80° C. for two hours, and complete conversion to MAO was confirmed by proton NMR analysis. Use of such catalytic quantities of preformed aluminoxane is unnecessary when the organic solvent/diluent employed is an inert liquid aromatic hydrocarbon such as toluene.

Example 6

Water-catalyzed reaction of a ketone with $R_3Al$ is exemplified by the reaction of benzophenone with TMA in toluene. Benzophenone (10 grams, 0.0549 mole) was dissolved in toluene (50 mL). Water (0.1 gram, 0.00549 mole) was added. Then TMA (7.91 grams, 0.1098 mole) was slowly added. The reaction was very exothermic and resulted in a slightly yellowish solution. A catalytic amount of solid MAO was added. Upon heating at 80° C. for 3 hours, the coloration disappeared and NMR showed complete conversion to MAO. The colorless product was found to be very active in ethylene polymerization. An attempt to use the intermediate product showed complete deactivation in ethylene polymerization.

Example 7

This experiment further illustrates an embodiment of the present invention wherein, unlike the prior art, no heat except for the natural exotherm was necessary to achieve complete conversion to MAO. Thus, TMA (10.24 grams, 0.142 mole) was allowed to react with a slurry of benzoic acid (5.4 grams, 0.04422 mole) in toluene (20.5 grams) containing water (0.08 gram, 0.004422 mole). After addition, the reaction flask was allowed to stand at room temperature for about one week. Surprisingly, proton NMR showed complete conversion to MAO. This basically allows the complete avoidance of the detrimental effect of heating with respect to gel formation. This MAO product is significantly less viscous compared to samples formed in the same way but by the addition of heat to the reaction mixture. This MAO product would also be expected to be more storage stable than MAO produced by application of heat to the reaction mixture.

Example 8

Figure 5:
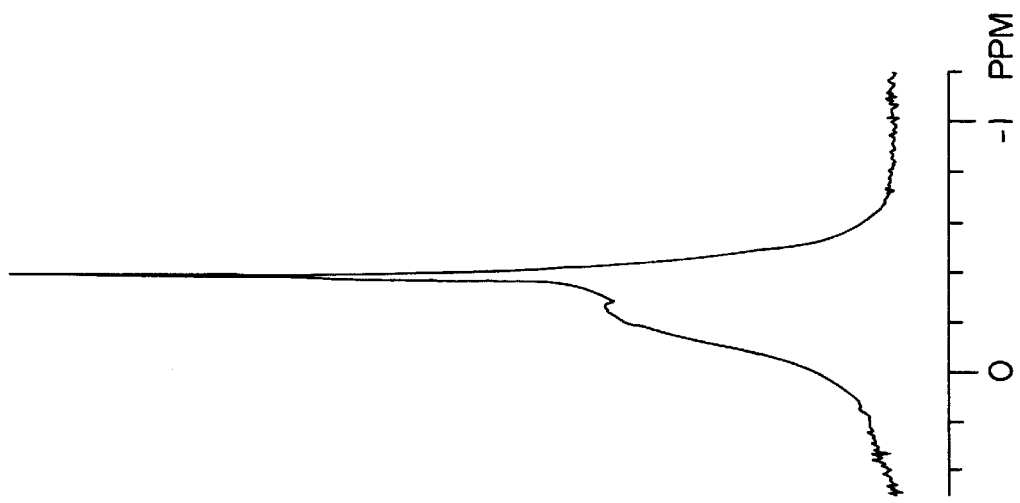
FIG. 5 is the Al—CH$_3$ region of a proton NMR spectrum of a reaction product formed in the same manner as that of FIG. 4 except that a catalytic quantity of water was added to the reaction mixture pursuant to this invention.
Figure 4:
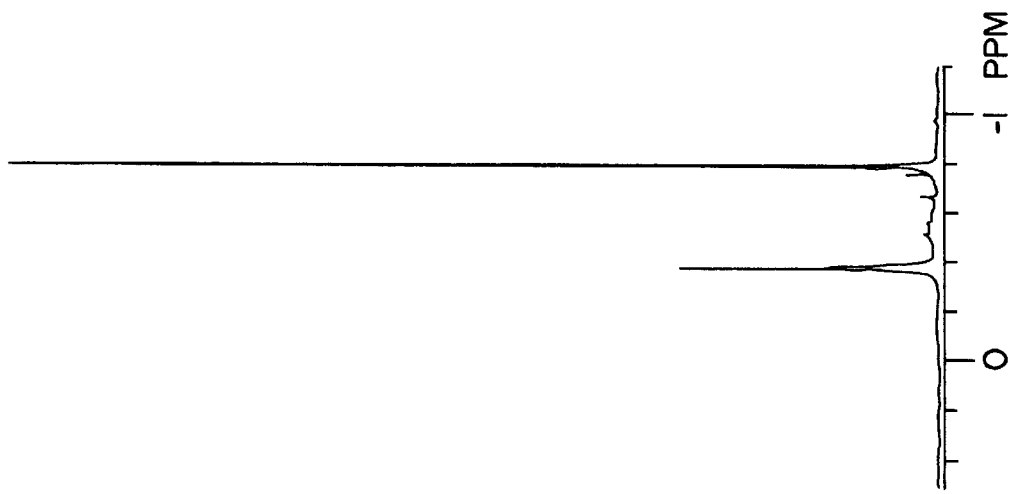
FIG. 4 is the Al—CH$_3$ region of a proton NMR spectrum of a reaction product formed without use of a catalytic quantity of water.

This Example illustrates by direct comparative experiments, the advantages of addition of a catalytic quantity of water in facilitating and accelerating the reaction of $R_3Al$ with carbonyl derivatives and in obtaining superior aluminoxane products of enhanced usefulness. Into each of two reaction tubes (tubes A and B) were placed benzophenone (BZA, 9.11 grams, 0.05 mole) and toluene (15 grams). In addition, a catalytic amount of water (0.09 gram, 0.005 mole) was added to the contents of tube B. Trimethylaluminum (5.41 grams, 0.075 mole) was slowly added to both tubes, with stirring at room temperature. Thus tube B represents a process of this invention whereas tube A represents a process of the prior art. The exothermic reactions resulted in clear yellowish solutions. On cooling to room temperature, both reactions gave a slurry of white precipitates. Then both tubes were heated at 80° C. (oil bath) for about two hours, during which time the solid precipitates dissolved to give a clear solution. On cooling, the contents of tube A again formed a slurry of white precipitates while the contents of tube B remained in solution. Substantial foaming was also observed in tube B. Proton NMR clearly showed that tube A (no water added) contained intermediate products (no significant amount of MAO product had been formed), but the content of tube B was completely transformed to an MAO composition (see NMR spectra, FIGS. 4 and 5).

Example 9

The MAO products prepared by the reaction of TMA with BZA in accordance with this invention were tested in ethylene polymerization using zirconocene dichloride without hydrogen addition. The catalyst activities were generally in the range of 400 to 600 kg of PE/gZr/hr, which compares well with similar tests for commercial MAO products.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or publication referred to in any portion of this specification is incorporated in toto into this disclosure by reference, as if fully set forth herein.

This invention is susceptible to considerable variation in its; practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process which comprises mixing together in the presence of an inert organic solvent or diluent and in the presence of a catalytic quantity of water, (I) a halogen-free alkylaluminum compound or a mixture thereof, and (ii) an organic carbonyl group-containing compound or mixture thereof, or carbon dioxide, or a combination of an organic carbonyl group-containing compound or mixture thereof and carbon dioxide such that an alkylaluminoxane product is produced.

2. A process according to claim 1 wherein (ii) is an organic carbonyl group-containing compound or mixture thereof, and wherein the weight ratio of the halogen-free alkylaluminum compound or mixture thereof to the inert organic solvent or diluent is in the range of about 20:80 to about 60:40.

3. A process according to claim 2 wherein (ii) is a ketone or mixture thereof.

4. A process according to claim 2 wherein (ii) is a non-enolyzable ketone or mixture thereof.

5. A process according to claim 2 wherein (ii) is a carboxylic acid or mixture thereof.

6. A process according to claim 2 wherein (ii) is a non-enolyzable carboxylic acid or mixture thereof.

7. A process according to claim 1 wherein (I) is trimethylaluminum.

8. A process according to claim 7 wherein the weight ratio of the trimethylaluminum to the inert organic solvent or diluent is in the range of about 30:70 to about 55:45.

9. A process according to claim 7 wherein the inert organic solvent or diluent is an inert liquid aromatic hydrocarbon solvent or diluent, and wherein the weight ratio of the trimethylaluminum to the inert liquid aromatic hydrocarbon solvent or diluent is in the range of about 40:60 to about 50:50.

10. A process according to claim 1 wherein the proportions of (I) and (ii) that are mixed together in the process are about 1.4 to about 2.2 moles of (I) per mole of oxygen atoms in (ii).

11. A process according to claim 2 wherein the catalytic quantity of water and the organic carbonyl group-containing compound or mixture thereof are co-present when (I) and (ii) are mixed together in the inert organic solvent.

12. A process according to claim 11 wherein the proportions of (I) and (ii) that are mixed together in the process are about 1.4 to about 2.2 moles of (I) per mole of oxygen atoms in (ii).

13. A process according to claim 12 wherein (I) is trimethylaluminum.

14. A process according to claim 1 wherein the reaction temperature is maintained below 100° C.

15. A process according to claim 1 wherein the reaction temperature is maintained in the range of about 60 to about 80° C. for a major portion of the reaction period.

16. A process according to claim 1 wherein the catalytic quantity of water does not exceed about 0.1 mole of water per mole of (ii).

17. A process according to claim 1 wherein (I) is trimethylaluminum, wherein (ii) is a ketone or mixture thereof, wherein the catalytic quantity of water and the ketone or mixture thereof are co-present when (I) and (ii) are mixed together in the inert organic solvent or diluent; wherein the weight ratio of the trimethylaluminum to the inert organic solvent or diluent fed to the reaction is in the range of about 30:70 to about 55:45; wherein the proportions of (I) and (ii) that are mixed together in the process are about 1.4 to about 2.2 moles of (I) per mole of oxygen atoms in (ii), and wherein the reaction temperature is maintained below 100° C.

18. A process according to claim 17 wherein the reaction temperature is maintained in the range of about 60 to about 80° C. for at least a major portion of the reaction period, and wherein the catalytic quantity of water does not exceed about 0.1 mole of water per mole of (ii).

19. A process according to claim 1 wherein (I) is trimethylaluminum, wherein (ii) is a carboxylic acid or mixture thereof, wherein the catalytic quantity of water and the carboxylic acid or mixture thereof are co-present when (I) and (ii) are mixed together in the inert organic solvent or diluent; wherein the weight ratio of the trimethylaluminum to the inert organic solvent or diluent fed to the reaction is in the range of about 30:70 to about 55:45; wherein the proportions of (I) and (ii) that are mixed together in the process are about 1.4 to about 2.2 moles of (I) per mole of oxygen atoms in (ii), and wherein the reaction temperature is maintained below 100° C.

20. A process according to claim 19 wherein the reaction temperature is maintained in the range of about 60 to about 80° C. for at least a major portion of the reaction period, and wherein the catalytic quantity of water does not exceed about 0.1 mole of water per mole of (ii).

21. A process according to claim 1 wherein the solvent or diluent consists essentially of a liquid aromatic hydrocarbon or mixture thereof.

22. A process according to claim 1 wherein the reaction is conducted adiabatically.

23. A process according to claim 22 wherein (I) is trimethylaluminum.

24. An alkylaluminoxane produced by the process of claim 1.

25. An alkylaluminoxane produced by the process of claim 17.

26. An alkylaluminoxane produced by the process of claim 19.

27. A process which comprises
   a) continuously feeding into a reactor (I) at least one aluminum trialkyl or alkyl aluminum hydride, or both, (ii) an organic carbonyl-group containing compound or mixture thereof, (iii) a catalytic quantity of water, and (iv) at least one inert organic solvent or diluent such that a reaction mixture comprising alkylaluminoxane or an intermediate precursor thereof is being produced in said reactor; and
   b) continuously or periodically withdrawing reaction mixture from the reactor at a rate sufficient to enable the continuous feed of a) into said reactor to be maintained.

28. A process according to claim 27 wherein the reator initially contains at least one inert organic solvent or diluent into which the continuous feeds of a) are introduced.

29. A process according to claim 27 wherein (I) and (iv) are fed together to the reactor as a solution or slurry in which the weight ratio of (I):(iv) is in the range of about 20:80 to about 60:40.

30. A process according to claim 27 wherein the temperature of the contents of said reactor is kept below 100° C.

31. A process according to claim 27 wherein the proportions of (I) and (ii) being fed to the reactor are about 1.4 to about 2.2 moles of (I) per mole of oxygen atoms in (ii).

32. A process according to claim 27 wherein the reaction is conducted adiabatically in said reactor.

33. A process according to claim 27 wherein (I) consists essentially of trimethylaluminum; wherein (ii) is a ketone or carboxylic acid; wherein (iv) consists essentially of an inert liquid paraffinic, cycloparaffinic, or aromatic hydrocarbon, or a mixture of any two or more of the foregoing hydrocarbons, wherein the weight ratio of (I):(iv) is in the range of about 30:70 to about 55:45; and wherein the proportions of (I) and (ii) being fed to the reactor are about 1.4 to about 2.2 moles of (I) per mole of oxygen atoms in (ii).

34. A process according to claim 33 wherein at least a major portion by weight of (iv) is one or more inert liquid aromatic hydrocarbons, and wherein the temperature of the contents of said reactor is kept below about 100° C.

35. A process according to claim 33 wherein (iv) consists essentially of one or more inert liquid aromatic hydrocarbons, and wherein the temperature of the contents of said reactor is kept below about 80° C. for a major portion of the reaction period.

36. A process according to claim 33 wherein the catalytic quantity of water being fed in a) does not exceed about 0.1 mole of water per mole of (ii) being fed in a).

37. A process according to claim 33 wherein (ii) is benzoic acid, a monoalkyl benzoic acid, a polyalkyl benzoic acid, or a combination of any two or more of the foregoing acids.

38. A process according to claim 33 wherein (ii) is benzoic acid.

39. A process according to claim 33 wherein (ii) is benzophenone, a monoalkyl-substituted benzophenone, a polyalkyl-substituted benzophenone, or a combination of any two or more of the foregoing benzophenones.

40. A process according to claim 33 wherein (ii) is benzophenone.

41. A process according to claim 27 wherein the reactor is a vessel into which the components of a) are continuously fed until the reactor has been filled to a predetermined level with the resultant reaction mixture, at which time the feeds of a) are discontinued, and thereafter all or at least a portion of the reaction mixture is withdrawn from the reactor.

42. A process according to claim 27 wherein
1) the reactor is a vessel into which the components of a) are continuously fed until the reactor has been filled to a predetermined level with the resultant reaction mixture, at which time the feeds of a) are discontinued;
2) the reaction mixture is withdrawn from the reactor;
3) the components of a) are again continuously fed into the reactor until the reactor has been filled to a predetermined level with the resultant reaction mixture, at which time the feeds of a) are discontinued;
4) the reaction mixture is withdrawn from the reactor; and
5) steps 3) and 4) are repeated sequentially as desired.

43. A process according to claim 27 wherein the reactor is a vessel into which the components of a) are continuously fed and from which the reaction product mixture is continuously withdrawn at a rate that is substantially equal to the rate at which the components of a) are continuously fed.

44. A process according to claim 27 wherein at least a portion of the catalytic quantity of water is continuously fed as a preformed mixture of water and said organic carbonyl group-containing compound or mixture thereof.

45. A process according to claim 27 wherein (I) consists essentially of one or more aluminum trialkyls; wherein (ii) is a ketone or carboxylic acid or mixture thereof; wherein (iv) consists essentially of one or more inert liquid aromatic hydrocarbons; wherein the weight ratio of (I):(iv) is in the range of about 30:70 to about 55:45; wherein the proportions of (I) and (ii) being fed to the reactor are about 1.4 to about 2.2 moles of (I) per mole of oxygen atoms in (ii); wherein the catalytic quantity of water being fed in a) does not exceed about 0.1 mole of water per mole of (ii) being fed in a); and wherein the temperature of the contents of said reactor is kept below about 80° C. for a major portion of the reaction period.

46. A process according to claim 45 wherein at least a portion of said catalytic quantity of water is continuously fed as a preformed mixture of water and said ketone or carboxylic acid or mixture thereof; and wherein said ketone or carboxylic acid or mixture thereof consists essentially of benzoic acid, a monoalkylbenzoic acid, a polyalkylbenzoic acid, a combination of any two or more of the foregoing acids, benzophenone, a monoalkyl-substituted benzophenone, a polyalkyl-substituted benzophenone, a combination of any two or more of the foregoing benzophenones, or a combination of one or more of the foregoing acids and one or more of the foregoing benzophenones.

47. A process which comprises
a) continuously feeding into a reactor (I) a solution composed of about 40 to about 50 percent by weight of trimethylaluminum in at least one inert liquid aromatic hydrocarbon, (ii) an organic carbonyl group-containing compound or mixture thereof, and (iii) a catalytic quantity of water such that a reaction mixture comprising a polymethylaluminoxane or an intermediate precursor thereof is being produced in said reactor, the proportions of (I) and (ii) being fed to the reactor being maintained such that there are about 1.4 to about 2.2 moles of trimethylaluminum per mole of oxygen atoms in said organic carbonyl group-containing compound or mixture thereof being fed, and the proportions of (ii) and (iii) being fed to the reactor being maintained such that there is in the range of about 0.001 to about 0.1 mole of water per mole of said organic carbonyl group-containing compound or mixture thereof being fed;
b) keeping the temperature of the reaction mixture within the reactor below about 100° C.; and
c) continuously or periodically withdrawing reaction mixture from the reactor at a rate sufficient to enable the continuous feed of a) into said reactor to be maintained.

48. A process according to claim 47 wherein said organic carbonyl group-containing compound or mixture thereof consists essentially of benzoic acid, a monoalkylbenzoic acid, a polyalkylbenzoic acid, or a combination of any two or more of the foregoing acids.

49. A process according to claim 48 wherein at least a portion of the catalytic quantity of water is continuously fed as a preformed mixture of water and the benzoic acid, monoalkylbenzoic acid, polyalkylbenzoic acid, or a combination of any two or more of the foregoing acids.

50. A process according to claim 49 wherein the temperature of the reaction mixture within the reactor is kept below about 80° C.

51. A process according to claim 47 wherein said organic carbonyl group-containing compound or mixture thereof consists essentially of benzoic acid, and wherein the catalytic quantity of water is continuously fed as a preformed mixture of water and benzoic acid.

52. A process according to claim 47 wherein in c) reaction mixture is continuously withdrawn from the reactor such that the rate of withdrawal in c) is substantially equivalent to the rate of the feeds in a).

53. A process according to claim 47 wherein in a) the feeds consist of (1) a solution of trimethylaluminum in a liquid mononuclear aromatic hydrocarbon solvent having at least 7 carbon atoms per molecule, and (2) a preformed mixture of water and an organic carbonyl group-containing compound or mixture thereof; and wherein in c) reaction mixture is continuously withdrawn from the reactor such that the rate of withdrawal in c) is substantially equivalent to the rate of the feeds in a).

54. A process according to claim 53 wherein the liquid mononuclear aromatic hydrocarbon solvent consists essentially of toluene, and wherein the organic carbonyl group-containing compound or mixture thereof consists essentially of benzoic acid.

55. A process according to claim 53 wherein the liquid mononuclear aromatic hydrocarbon solvent consists essentially of toluene, and wherein the organic carbonyl group-containing compound or mixture thereof consists essentially of benzophenone.

56. A process which comprises concurrently feeding into a reactor (I) at least one aluminum trialkyl or alkyl aluminum hydride, or both, (ii) an organic carbonyl-group containing compound or mixture thereof, and (iii) a catalytic quantity of water in proportions such that there are about 1.4 to about 2.2 moles of (I) being fed per mole of oxygen atoms in (ii) being fed, and such that there is in the range of about 0.001 to about 0.1 mole of (iii) being fed per mole of (ii) being fed.

57. A process according to claim 56 wherein the reactor initially contains at least one inert organic solvent or diluent into which the concurrent feeds are introduced, and wherein the temperature of the reaction mixture within the reactor is kept below about 100° C.

58. A process according to claim 56 wherein (I) is trimethylaluminum; and wherein (ii) is benzoic acid, a monoalkylbenzoic acid, a polyalkylbenzoic acid, a combination of any two or more of the foregoing acids, benzophenone, a monoalkyl-substituted benzophenone, a polyalkyl-substituted benzophenone, a combination of any two or more of the foregoing benzophenones, or a combination of one or more of the foregoing acids and one or more of the foregoing benzophenones.

59. A process according to claim 56 wherein (I) is trimethylaluminum; wherein (ii) is benzoic acid or benzophenone; and wherein the temperature of the reaction mixture within the reactor is kept below about 80° C.

* * * * *